(12) United States Patent
Valerio et al.

(10) Patent No.: US 6,261,554 B1
(45) Date of Patent: Jul. 17, 2001

(54) COMPOSITIONS FOR TARGETED GENE DELIVERY

(75) Inventors: Domenico Valerio, Leiden; Victor Willem van Beusechem, Amsterdam, both of (NL)

(73) Assignee: Introgene B.V., Leiden (NL)

( * ) Notice: Subject to any disclaimer, the term of this patent is extended or adjusted under 35 U.S.C. 154(b) by 0 days.

(21) Appl. No.: 09/000,133

(22) PCT Filed: Jul. 25, 1996

(86) PCT No.: PCT/NL96/00302

§ 371 Date: Feb. 24, 1998

§ 102(e) Date: Feb. 24, 1998

(87) PCT Pub. No.: WO97/05266

PCT Pub. Date: Feb. 13, 1997

(30) Foreign Application Priority Data

Jul. 25, 1995 (EP) .................................................. 95202040

(51) Int. Cl.⁷ .......................... A61K 35/00; A61K 48/00; C12N 15/63; C12N 15/85
(52) U.S. Cl. ..................... 424/93.6; 435/320.1; 435/455; 514/44
(58) Field of Search ................................ 435/320.1, 455; 514/44; 424/93.6

(56) References Cited

U.S. PATENT DOCUMENTS

| 6,033,908 | 3/2000 | Bout et al. . |
| 6,040,174 | 3/2000 | Imler et al. . |

FOREIGN PATENT DOCUMENTS

| 0496074 | 7/1992 | (EP) . |
| 2649119 | 1/1991 | (FR) . |
| WO/9222332 | 12/1992 | (WO) . |
| WO/9309221 | 5/1993 | (WO) . |
| WO/9412626 | 6/1994 | (WO) . |
| WO/9416734 | 8/1994 | (WO) . |
| WO/9526412 | 10/1995 | (WO) . |
| WO 97/00326 | 1/1997 | (WO) . |

OTHER PUBLICATIONS

Orkin, SH and Motulsky, AG Report and recommendations of the panel to assess the NIH investment in research on gene therapy, Dec. 1995.*

Friedmann, T. Overcoming the obstacles to gene therapy. Sci. Am. Jun. 1997 pp. 96–101.*

Verma et al. Gene therapy—promises, problems, and prospects. Nature 389: 239–242, Sep. 1997.*

Boado R.J (1995) *Adv. Drug Deliv. Rev.*, 15:73–107.

Curiel et al. (1994) *Virology*, 198:577–585.

Etienne–Julian et al. (1992) *J. Gen. Virol.*, (1992) 73: 3251–3255.

Marin et al. (1994)*Gene Therapy*, 1(2):s15.

Nilson et al. (1994) *Gene Therapy*, 1(2):s17.

Roux et al. (1989) *Proc. Natl. Acad. Sci.*, 86:9079–9083.

Russell et al. (1993) *Nucleic Acids Research*, 21(5):1081–1085.

Truong et al. (1993) *Proc. Intern. Symp. Control. Release Bioact. Mater.*, 20:474–475.

Zatloukal et al. (1993) *J. Cell Biochem.*, 17(d):129.

* cited by examiner

*Primary Examiner*—Karen M. Hauda
*Assistant Examiner*—Anne-Marie Baker
(74) *Attorney, Agent, or Firm*—TraskBritt (57) ABSTRACT

A method of producing viral gene delivery vehicles which can be transferred to pre-selected cell types by using targeting conjugates. The gene delivery vehicles comprise: 1) the gene of interest; 2) a viral capsid or envelope carrying a member of a specific binding pair, the counterpart of which is not directly associated with the surface of the target cell. These vehicles can be made unable to bind to their natural receptor on the cell. The targeting conjugates are composed of the counterpart member of the specific binding pair linked to a targeting moiety which is a cell-type specific ligand. The number of the specific binding pair present on the viral vehicles can be, for example, an immunoglobulin binding moiety, biotin, avidin, or streptavidin. The outer membrane or capsid of the virus may contain a substance which mediates entrance of the gene delivery vehicle into the target cell. Due to the specificity of the ligand, the high affinity of the binding pair and to the inability of the gene delivery vehicle to be targeted when used alone, the universality of the method for gene delivery, together with its high cell type selectively can easily be achieved by the use of various adequate targeting conjugates.

1 Claim, 5 Drawing Sheets

COMPOSITIONS FOR TARGETED GENE DELIVERY

FIELD OF THE INVENTION

The present invention relates to the field of providing cells with additional genetic information through recombinant DNA techniques. It especially relates to methods and means of providing specific groups of cells with additional genetic information, in particular in the context of gene therapy.

Gene therapy is a recently developed concept which has a very broad range of applications, ranging from supplementing deficiencies in a mammals' set of proteins, usually resulting from genetic disorders, to the treatment of cancer, (auto-)immune diseases or (viral) infections, usually by eliminating or suppressing the responsible set of cells or organisms.

One of the main problems in gene therapy is delivering the genetic material to the target cells and not to other cells. Another problem in gene therapy is that certain cell types are extremely refractory to current gene transfer techniques.

The present invention relates generally to gene delivery vehicles and their use in gene therapy, and more particularly, to recombinant viruses which can be targeted to susceptible target cells.

Retroviruses are RNA viruses which efficiently integrate their genetic information into the genomic DNA of infected cells via a reverse-transcribed DNA intermediate. This property of their life-cycle and the fact that parts of their genetic material can be replaced by foreign DNA sequences make retroviruses one of the most promising vectors for the delivery of genes in human gene therapy procedures, most notably for gene therapies which rely on gene transfer into dividing tissues. Most retroviral vector systems are based on mouse retroviruses and consist of two components, i.e. (i) the recombinant retroviral vector carrying the foreign sequences of interest, and (ii) so-called packaging cells expressing the structural viral proteins of which the encoding sequences are lacking in the retroviral vector. Expression of (i) in (ii) results in the production of recombinant retroviral particles capable of transducing susceptible target cells.

The infectivity and host cell range of the retrovirus particle is conferred by an envelope glycoprotein which specifically binds to a receptor molecule on the target cell membrane. The envelope glycoprotein of all known retroviruses consists of two associated peptides, which are derived by proteolytic cleavage from the same precursor protein encoded by the retroviral env gene (Dickson et al. in Weiss et al. (ed.) Molecular biology of tumor viruses (1984), Cold Spring Harbor Press, pp. 513–648). The amino terminal peptide encompasses the specific binding site for its receptor on the target cell membrane, thus determining the virus host range (Hunter and Swanstrom, Curr. Top. Microbiol. Immunol. 157(1990): 187). The carboxy terminal peptide, which contains trans-membrane anchor sequences, is assumed to account for the selective uptake of the envelope glycoprotein in the virus particle and to mediate fusion between the virus membrane and—depending on the type of virus—the plasma membrane or intracellular vesicle membrane of the target cell.

Several envelope glycoprotein variants with different infection spectra for mammalian cells have been identified. All known env variants have a rather broad infection spectrum in common. Here lies one of the major shortcomings of current recombinant retrovirus technology. In numerous gene therapy applications targeted delivery of genes into defined cells would be desired, most notably in the case of in vitro gene transfer into cell types present with low abundance in cell mixtures and in approaches for in vivo gene transfer into cells in a living mammalian body. Conventional gene transfer techniques have the disadvantage in such applications of low efficiency of gene transfer to desired target cells, because the gene transfer vehicles are taken up by other cells as well. In addition, the cell mixture or living mammalian body may contain cells to which gene transfer is absolutely undesired. E.g., genes providing protection against chemotherapeutic drugs should not be transferred into malignant cells. Therefore, increasing attention is focused on devising procedures to limit the retrovirus infection spectrum. By employing particular env variants the transduction spectrum can be limited to some extend, but true specificity for most target cells of interest can not be obtained this way. On the other hand, on the surface of some specific cell types the expression of receptors for retroviral entry is extremely low. An important example of a cell type with low retrovirus receptor expression is the pluripotent stem cell of the hematopoietic system (Orlic et al., Blood 86 suppl 1 (1995): 628a). A preferred strategy to accomplish targeted delivery is to direct the retrovirus particle to cell membrane molecules differing from the natural envelope glycoprotein receptor, said molecule being specifically expressed on the membrane of the desired target cell. Present ideas about how this could be done include:

1. direct chemical coupling of a ligand for a target cell molecule to the viral envelope glycoprotein (Neda et al, J. Biol. Chem. 266(1991): 14143),
2. bridging the viral envelope glycoprotein to a molecule on the target cell through a complex of two antibodies, one directed against the viral envelope glycoprotein and the other against the molecule on the target cell (Goud et al., virology 163(1988): 251; Roux et al., Proc. Natl. Acad. Sci. USA 86(1989): 9079; Etienne-Julan et al., J. Gen. Virol. 73(1992): 3251),
3. bridging the viral envelope glycoprotein to a molecule on the target cell through a complex of an antibody directed against the viral envelope glycoprotein and a peptide ligand for the molecule on the target cell (Etienne-Julan et al., J. Gen. Virol. 73(1992): 3251)
4. replacing the specific binding site of the viral envelope glycoprotein for its receptor by a peptide ligand for a target cell surface molecule,
5. co-expression on the virus membrane of the natural viral envelope glycoprotein and a ligand for a target cell surface molecule (Young et al., Science 250(1990): 1421), and
6. co-expression on the virus membrane of the natural viral envelope glycoprotein and an altered viral envelope glycoprotein in which the specific binding site for its receptor has been replaced by a peptide ligand for a target cell surface molecule (Young et al., Science 250(1990): 1421; Russell et al., Nucl. Acid Res. 5(1993): 1081; Chu et al., Gene Ther. 1(1994): 292; Kasahara et al., Science 266 (1994): 1373; Chu and Dornburg, J. Virol. 69(1995): 2659).

Monoclonal antibodies or fragments thereof, exhibiting high specificity and affinity for the target cell specific molecule, are amongst the preferred ligands for targeted delivery. Approaches nos. 2 and 3 mentioned above rely on antibodies and promising tools for use in the approaches nos. 4 and 6 are chimaeric molecules between viral envelope glycoproteins and single-chain antibody fragments of the variable antigen-binding domain of immunoglobulins (scFv) (Russell et al., Nucl. Acid Res. 5(1993): 1081; Chu et al., Gene Ther. 1(1994): 292; Chu and Dornburg, J. Virol.

69(1995): 2659). A chimaeric molecule of such an scFv fragment and a different membrane anchoring protein than the viral envelope glycoprotein could be used for approach no. 5.

An important limitation of all these previously invented approaches is that a new virus with a specific targeting ligand (chemically or genetically modified envelope glycoprotein, or co-expressed ligand) or a new specific dual-antibody complex has to be made for each target cell type. The present invention bypasses this limitation.

Adenovirus capsids are regular icosahedrons composed of 252 subunits, of which 240 are so-called hexons and 12 are so-called pentons. The pentons are located at the vertices of the icosahedron. They contain a penton base on the surface of the capsid which is composed of five molecules of a 85 kD polypeptide. A fiber composed of a homotrimer of 62 kD polypeptides projects from the penton base outward. The fiber protein is responsible for attachment of the adenovirus to its receptor (reviewed by Horwitz, in: Virology, 2nd edition (Fields et al, ed), Raven Press, New York, 1990, pp. 1679–1721). By exchanging fiber protein domains from two adenoviruses of different serotype, Stevenson et al. (J. Virol. 69(1995): 2850) have shown that the receptor specificity is determined by the head domain of the fiber protein.

The adeno-associated virus (AAV) capsid is comprised of three viral proteins (VP): VP-1, VP-2, and VP-3. These proteins have molecular masses of 87 kD, 73 kD, and 62 kD, respectively. In mature virions VP-1, VP-2 and VP-3 are found at relative abundance of approximately 1:1:10. In vitro,. the three proteins assemble spontaneously into virion-like structures. It appears, therefore, that capsid formation in infected cells proceeds independent of viral DNA synthesis (reviewed by Kotin, Hum. Gene Ther. 5(1994): 793). It has been shown possible to insert sequences into the genes encoding the capsid proteins, resulting in the exposure of His-residues on the surface of intact AAV capsids. Consequently, these altered AAV virions were able to bind to a nickel-column (unpublished results from the group of Dr. R. Samulski, Univ. of North Carolina, Chapel Hill, N.C.). The present invention makes use of the possibility to insert sequences in said capsid genes.

The present invention thus provides a gene delivery vehicle for delivering genetic material to a target cell, comprising an expressable recombinant nucleic acid molecule encoding a gene product of interest, a capsid or an envelope derived from a virus, and a member of a specific binding pair, the counterpart of which is not directly associated with the surface of the target cell.

This gene delivery vehicle itself is preferably incapable of specifically binding to a target cell, meaning that it is no longer an infectious virus particle. Instead of having its regular infectivity it is provided with a member of a specific binding pair, either as a part of its envelope or as a part of its capsid. This gene delivery vehicle in itself cannot be targeted to a target cell, but it is a novel and inventive intermediate in the process of preparing a targeting gene delivery vehicle, which together with a targeting component is capable of delivering a gene to target cells only, or at least of delivering genes to the target cells in a far greater amount than to non-target cells (or other targets, such as infectious organisms), or of delivering a gene to cells previously difficult to transduce as a result of low viral receptor expression. The invention thus also provides a targeting component which is a conjugate for use in targeting a gene delivery vehicle as disclosed above to a target cell, which conjugate comprises the counterpart of the member of a specific binding pair (which member is present on or in the gene delivery vehicle, which counterpart is coupled to a targeting moiety being capable of binding to a target molecule associated with the surface of a target cell.

Thus the conjugate has dual specificity. On the one side the counterpart recognizes the member of a specific binding pair present on or in the gene delivery vehicle and on the other side it recognizes a target molecule associated with the surface of the target cell. When such a conjugate is coupled to a gene delivery vehcle a targeting gene delivery vehicle is obtained. Thus the invention also provides a targeting gene delivery vehicle, comprising a gene delivery vehicle according as disclosed hereinabove, coupled to a conjugate according also described above.

The main advantage of the gene delivery vehicles according to the invention is that they have a recognizable moiety, which is independent from the target cell the genes have to be delivered to. This means that they can be targeted to many different target cells, by using different conjugates which all recognize the vehicle (a constant part of the conjugate) and which recognize a number of different targets associated with target cells on the other side. Thus the gene of interest can be delivered to many different cells, without having to prepare a new vehicle.

A similar approach has been disclosed and is described above as approach no. 3. In this approach however, the vehicle has not been provided with an additional member of a specific binding pair, but a viral antigen (the envelope glycoprotein) itself is the member of a specific binding pair being recognized by an antibody. Apart from the drawback of having to make a new specific dual-antibody complex for every delivery system, an even more important drawback is that all antigens have to be bound to an antibody, because otherwise the vehicle will retain its capability of infecting its regular host cells, whereas for the gene delivery vehicles according to the invention these glycoproteins are preferably (if not necessarily) not present or altered to impair their normal function.

In the following it will become clear that preferred embodiments of the present invention are so called kits (kits of parts) which provide a gene delivery vehicle as one part and at least one targeting moiety as another part.

Another part of the invention therefor is a kit of parts for delivering genetic material to a target cell, comprising a gene delivery vehicle according to the invention and at least one conjugate of the counterpart member of the specific binding pair coupled to a targeting moiety, said targeting moiety being capable of binding to a target molecule associated with the surface of a target cell.

The embodiments given above are the general formats of the invention. Thus it is clear that as well a gene delivery vehicle itself, as well as a conjugate, the delivery vehicle coupled to a conjugate and the kit in which both conjugate and delivery vehicle all can be adjusted to the specific embodiments which are recited for the kits only. Thus the specific conjugates without the delivery vehicle and the specific vehicles without the conjugates as well as the specific targeting vehicles are part of this invention as well. For example where a kit of parts is disclosed comprising as a member an immunoglobulin binding protein and as its counterpart an immunoglobulin, this means that the conjugate comprising the immunoglobulin is part of the invention as is the gene delivery vehicle comprising the immunoglobulin binding protein.

The definitions in the claims are themselves clearly understood in the art.

Specific binding pairs for instance are considered to be any two molecules which have a high affinity specific interaction between the two members (herein often referred to as the member and its counterpart). These may be antibody (fragments or derivatives) and the corresponding antigen, receptors and their ligands (in this case especially proteinaceous ligands), well known binding pairs such as avidin/biotin or streptavidin/biotin, peptide structures that can specifically interact in solution and the like. In many instances members of these binding pairs will not be normally present in the envelope or the capsid of a virus and will thus also not be normally present on the gene delivery vehicles according to the invention, For that purpose they may have to be modified in a suitable manner, for instance chemically, or they may need to be present as fusion molecules or hybrid molecules linked to a component which ensures their presence in or on the capsid or envelope. As long as they still have the same function (in kind not in amount) as the original member of the binding pair (i.e. they still bind the counterpart) they should be considered as being a derivative or equivalent of the original member of the binding pair and are thus paret of the present invention. The same goes for the counterpart of the member of the specific binding pair and also for the targeting moiety, which is the other side of the conjugate.

Hereinunder a number of possibilities of providing a capsid or an envelope with the function of a member of a specific binding pair are given, exemplified for the preferred vehicles, but skilled artisians will be able to transfer these teachings to other vehicles and/or other members of specific binding pairs as well as other methods of providing these members on envelopes and/or capsids without departing from the present invention.

A conjugate is defined for the purposes of the present invention as Any molecule which has at least two different specific recognition sites, which are somehow linked. This means that it does not necessarily include chemical coupling or fusion proteins, although these are conjugates according to the invention, but that it also includes molecules which normally have this double specific recognition, such as for instance antibodies which recognize an antigen specifically and of which the constant region is specifically recognized by for instance Fc receptors. A nucleic acid encoding a gene of interest should be interpreted as not only encoding proteins, but also antisense nucleic acids and other useful nucleic acids, although these are not usually considered to be genes. When the nucleic acids do encode proteins there are many known genes of interest in the field, particularly in the field of gene therapy. All these genes can be delivered to target cells using the methods and means of the present invention. Of particular interest are suicide genes, such as Herpes Simplex Virus Thymidine Kinase and others disclosed in WO 93/07281.

The target cells to which the genes of interest can be delivered are basically any target cells that have a target molecule associated with their surface with which it is possible to distinguish them from other cells using a targeting moiety. The ability to distinguish may lie in the abundance of a certain target molecule on a certain subset of cells. Furthermore, it is not necessary for the application of the invention that the nature of the target molecule is known. Targeting moieties can be selected from combinatorial peptide libraries on the basis of differential binding to molecules expressed on the surface of different cell types. Useful combinatorial peptide libraries for the invention include those in which a large variety of peptides is displayed on the surface of filamentous bacteriophages (e.g. Scott and Smith, Science 249(1990): 386). Screening for individual library members that interact with desired target cells allows the isolation of the nucleotide sequences encoding suitable peptide structures to be used as a targeting moiety in the invention. For this purpose, libraries displaying scFv variants are particularly useful. Moreover, methods that increase the combinatorial diversity of said libraries make the number of targeting moieties that can be generated for application in the invention almost limitless. Said methods include PCR-based random mutagenesis techniques (Stemmer, Proc. Natl. Acad. Sci. USA 91(1994): 10747; Crameri and Stemmer, Biotechniques 18(1995): 194). Thus it is understood from the above that the invention discloses methods for specific gene delivery into any target cell that can be phenotypically distinguished from other cells, also when the nature of this distinction has not been revealed. Important target cells are tumor cells, cells of the hematopoietic system, hepatocytes, endothelial cells, lung cells, cells of the central nervous system, muscle cells and cells of the gastrointestinal tract. Usual target molecules are receptors, surface antigens and the like.

As indicated above the invention also includes a kit of parts wherein the member of a specific binding pair is an immunoglobulin binding moiety and its counterpart is an immunoglobulin or a derivative or a fragment thereof.

Preferably the immunoglobulin binding moiety is capable of binding to a constant region of an immunoglobulin. A much preferred immunoglobulin binding moiety is protein A, protein G, or an Fc receptor. One of the most commonly used immunoglobulin-binding proteins is *Staphylococcus aureus* protein A. This 42 kD polypeptide exhibits strong binding to the Fc region of many IgG molecules, including human IgG1, IgG2 and IgG4 and mouse IgG2a and IgG2b, without interfering with the antigen binding site (Surolia et al., Trends Biochem. Sci. 7(1981): 74; Lindmark et al, J. Immunol. Meth. 62(1983): 1). A wider range of mammalian immunoglobulins is bound by protein G, which is isolated from a group C Streptococcus species. It has strong binding capacity for all human and mouse IgG subclasses (Bjork and Kronvall, J. Immunol. 133(1984): 969; Sjöbring et al., J. Biol. Chem. 266(1991): 399). Protein A and G do not intrinsically bind to mammalian cell surfaces or virus membranes or capsids. Expression of (parts of) these molecules on the surface of gene delivery vehicles will therefore require the generation of hybrid molecules. A hybrid between streptavidin and two of the IgG binding domains of protein A has been made and bound one IgG molecule per hybrid (Sano and Cantor, Bio/Technol. 9(1991): 1378).

The mammalian receptors for the Fc domain of immunoglobulins (FcR), however, are trans-membrane molecules (reviewed by van de Winkel and Capel, Immunol. Today 14(1993): 215). These receptors provide a feedback between the humoral and cellular immune responses. Their interaction with immunoglobulins triggers immune functions such as phagocytosis, cytotoxicity, cytokine release and enhancement of antigen presentation. FCR are members of the immunoglobulin superfamily and in humans three classes of receptors for the Fc domain of IgG (FcgR) are recognized (hFcgRI, hFcgRII, and hFcgRIII). hFcgRI is unique in its capacity to bind with high affinity to monomeric IgG (Ka= $10^8$–$10^9$ M$^{-1}$). Its binding is strong to human IgG3, IgG1, and IgG4 (with decreasing affinity), and to mouse IgG2a and IgG3, whereas human IgG2 and mouse IgG1 and IgG2b are bound much weaker. hFcgRI is constitutively expressed on monocytes and macrophages and its expression can be induced on neutrophils and eosinophils. Three highly homologous genes for hFcgRI have been identified. Of these, hFcgRIA encodes a trans-membrane molecule, hFcgRIa (a-chain), consisting of three extracellular immunoglobulin-like domains (one of which is not found among other members of the hFcgR-family), a 21 amino acid trans-membrane region, and a charged cytoplasmic tail of 61 amino acids. On the membrane of some cell types the hFcgRIa a-chain is found associated with a disulfide-linked homodimer of g-chains, which are also components of other members of the FcR family (Scholl and Geha, Proc. Natl. Acad. Sci. USA 90(1993): 8847). There exists some controversy whether the presence of g-chains is absolutely essential for membrane expression and ligand binding of the hFcgRIa a-chain (Takai et al, Cell 76(1994): 519). The signal transduction after immunoglobulin binding to the a-chain into the interior of the cell is mediated by the g-chains; the cytoplasmic domain of the a-chain does not seem to play a role in signal transduction (Indik et al, Exp. Hematol. 22(i994): 599).

Because the constant regions of immunoglobulins differ between species, anti-immunoglobulin antibodies can be generated by cross-species immunization. For several species antibodies have been raised which show specificity to individual immunoglobulin chains or even subclasses. Molecular cloning of the sequences encoding these antibodies offers the possibility to construct scFv, which comprise of the variable regions of the heavy and light chains of the immunoglobulin molecule linked by a flexible peptide bridge. Such scFv have been shown to be as potent in antigen binding as are immunoglobulin Fab fragments (Bird et al, Science 242(1988): 423). Hybrid molecules between scFv and virus envelope molecules have been made and expressed on the surface of mammalian cells and were shown to be capable of antigen binding and targeted gene delivery (Chu et al, Gene Ther. 1(1994): 292; Chu and Dornburg, J. Virol. 69(1995): 2659).

When the gene delivery vehicle is provided with an immunoglobulin binding moiety, only a suitable antibody (or a derivative or a fragment(retaining the binding site for the immunoglobulin binding protein)) is needed as the entire conjugate. Thus, when an antibody is available which can distinguish a target cell from other cells, the gene delivery vehicle is ready to be used to target the gene of interest to said cell using said antibody. Thus for any cell which can be distinguished from other cells using antibodies, a targeted gene delivery system is provided.

The same is true for another embodiment of the present invention, in which the member of a specific binding pair is biotin and its counterpart is avidin or streptavidin, or in which the member of a specific binding pair is avidin or strepatavidin and its counterpart is biotin. In this embodiment the delivery vehicle is provided with the one member of the (strept)avidin/biotin couple and thus the conjugate comprises the other member.

Thus any targeting moiety that can be biotinylated or can be coupled to (strept)avidin is now usable with the gene delivery vehicle according to the present invention. This makes the number of targeting moieties that can be applied almost limitless. Any molecule associated with the surface of a target cell for which a specific binding partner is known or can be produced is in principle useful as a target for the presently invented gene delivery system, if in presence or abundance it differs from one subset of cells to another. Antibodies of course are a good example of suitable targeting moieties of this last embodiment, as they were for the embodiment before that. Thus a preferred embodiment of the present invention encompasses a kit of parts wherein the targeting moiety is an antibody or a fragment or a derivative thereof, recognizing the target molecule associated with the surface of the target cell.

Another group of suitable targeting moieties are ligands wherein the target molecule is a receptor (for which the targeting moiety is a ligand) associated with the surface of the cell.

For many cell type-specific antigens protein ligands have been identified which bind with high specificity and/or affinity, e.g. cytokines binding to their cellular receptors. Most proteins can be labeled with the water-soluble vitamin biotin, using simple procedures. Most biotinylations are performed using succinimide esters of biotin. Binding to the protein proceeds through free amino groups, normally of lysyl residues. Biotinylated molecules are bound with exceptionally high affinity ($Ka=10^{14}-10^{15}$ $M^{-1}$) by both Avidin and Streptavidin (Wilchek and Bayer, Immunol. Today 5(1984): 39). Avidin is a 68 kD glycoprotein isolated from egg white and Streptavidin is a 60 kD protein from *Streptomyces avidinii*. Both molecules are homotetramers; each subunit contains a single biotin binding-site. The high affinity of their binding makes the biotin-avidin or biotin-streptavidin interactions essentially irreversible. A functional streptavidin gene has been cloned (Sano and Cantor, Proc. Natl. Acad. Sci. USA 87(1990): 142) and a streptavidin mutant has been generated (Sano and Cantor, Proc. Natl. Acad. Sci. USA 92(1995): 3180) with reduced biotin-binding affinity (approx. $Ka=108$ $M^{-1}$) providing specific and tight, yet reversible biotin-binding. As for Protein A and G, avidin and streptavidin do not intrinsically bind to mammalian cell surfaces or virus membranes or capsids. Expression of (parts of) these molecules on the surface of gene delivery vehicles will therefore also require the generation of hybrid molecules. Hybrids of streptavidin and heterologous proteins have been made and retained full biotin binding capacity (Sano and Cantor, Bio/Technol. 9(1991): 1378; Sano et al., Proc. Natl. Acad. Sci. USA 89(1992): 1534).

In yet another embodiment of the invention the member of the specific binding pair and its counterpart are both peptides forming three-dimensional structures that can interact in solution. Peptides useful in this aspect of the invention include but are not restricted to dimerization motifs that are identified within proteins known to form dimers, such as the yeast transcription factor GCN4, the mammalian transcription factor C/EBP, and the nuclear transforming oncogene products fos, jun, and myc. Alternatively, synthetic peptides can be used that are designed on the basis of the knowledge of inter and intra protein interactions. The paradigm of peptide motifs known to dimerize is the coiled-coil structure, a subset of which is the so called leucine zipper (Landschultz et al., Science 240(1988)1759; O'Shea et al., Science 243(1989): 538; O'Shea et al., Science 254(1991): 539). Several proteins containing a leucine zipper motif can not only form homodimers but also heterodimers (Hai et al., Genes & Dev. 3 (1989): 2083; Roman et al., Genes & Dev. 4(1990): 1404). The leucine zipper dimerization region itself contains all of the structural information determining the dimerization specificity (Agre et al., Science 246(1989): 922; Kouzarides and Ziff, Nature 340(1989);568; O'Shea et al., Science 245(1989): 646). For the design of the member of the specific binding pair and its counterpart in the present invention it is preferred that the peptides used preferentially, if not exclusively, form heterodimers and not homodimers. Vinson et al (Genes & Dev. 7(1993): 1047) have proposed and verified a rule for the rational design of leucine zipper motifs at preferentially form heterodimers. Therefore, it is preferred that the peptides used in this aspect of the invention are designed according to this so called "i+5 salt bridge" rule. Expression of a dimerizing peptide motif on the surface 
of the delivery vehicle as well as conjugation of its dimerizing counterpart to the targeting moiety will require the generation of hybrid molecules. Many different hybrid proteins with functional leucine zipper domains have already been produced, including dimeric antibodies based on scFv (Pack and Plückthun, Biochemistry 31(1992): 1579), dimeric antibodies based on monoclonal Fab' fragments (Kostelny et al., J. Immunol. 148(1992): 1547), and a set of heterodimerizing proteins with leucine zippers, one linked to phagemid pIII coat protein and the other linked to the products from a cDNA library, that can be used for the production of a combinatorial phagemid cDNA library (Crameri and Suter, Gene 137(1994): 69).

When the gene delivery vehicle is provided with a peptide structure capable of dimerization with a counterpart in solution it can be used in combination with any targeting moiety that can be coupled to said counterpart. Using standard techniques known in the art expression constructs can be made for insertion of foreign sequences resulting in the translation of fusion proteins containing a leucine zipper terminal domain. Said coupling may either be direct or via an intervening linker sequence separating the individual folding domains of said targeting moiety and counterpart. Linker sequences known in the art that provide the peptide main chain with conformational freedom, thereby separating individual folding domains, are usually rich in glycine residues. Examples of linker peptide sequences useful in the invention include but are not restricted to $(Gly_4\text{-}Ser)_3$ (Batra et al., J. Biol. Chem., 265(1990): 15198) and $(Gly_4\text{-}Thr)_3$ (Bird et al., Science 242(1988): 423). It is thus understood from the above that also in this aspect of the invention the number of targeting moieties that can be applied is almost limitless.

As stated above it is possible to target the gene delivery vehicles to many different cells using different conjugates (antibodies, biotinylated targeting moieties or targeting moieties conjugated to a peptide structure that can interact in solution). It is thus preferred to provide a kit of parts according to the invention comprising a multitude of different conjugates, comprising the same counterpart member but a number of different targeting moieties.

Although as stated above the skilled artisan will be able to apply the teaching of the present invention to other viruses than those exemplified herein, the exemplified viruses are preferred embodiments, because of the experience with the viruses in gene therapy concepts. Retroviruses are especially suitable for gene transfer into replicating cells. Foreign genes introduced by retroviruses become stable components of the genome of the target cell and its progeny. Adenoviruses, on the other hand, efficiently introduce foreign genetic material into non-dividing target cells. Adeno-associated virus is the only currently known non-pathogenic DNA-virus. It could provide an alternative for both retroviruses and adenoviruses in certain gene transfer applications. Thus it is preferred that the gene delivery vehicle is derived from an adenovirus, an adeno associated virus or a retrovirus.

BRIEF DESCRIPTION OF THE DRAWINGS

FIG. 1 depicts the specific binding of biotinylated G-CSF to mouse fibroblasts expressing DG-CSFR on their membrane. FACS histograms of biotinylated G-CSF binding (log scale) are given. Solid lines represent measurement after incubation in biotinylated G-CSF, PE-Streptavidin, biotinylated goat-anti-Streptavidin, and PE-Streptavidin. Broken lines represent results of control incubations without biotinylated G-CSF. The percentage of cells showing specific binding of biotinylated G-CSF is shown in the upper right corner of each panel. Panel A: unmanipulated mouse fibroblasts, panel B: mouse fibroblasts transduced with LNCX-GRDcyt virus and selected with G418, panel C: mouse fibroblasts transduced with LNCX-GRDcyt virus, selected with G418, FACS sorted for GRDcyt expression and cloned by limiting dilution.

FIG. 3 depicts the structure of the two hybrid hFcgRIa/Mo-MuLV env molecules and their parental hFcgRIa and Mo-MuLV env proteins. The Mo-MuLV env peptides gp70 and p15E which are formed by proteolytic cleavage are shown separately and their physical connection on the precursor peptide is delineated by a broken line. Numbers above different segments indicate number of aminoacids. Asterisks indicate position of Cys-residues. Arrows represent primers used for PCR amplification. Areas in FcRenv-15 and FcRenv-70 indicated with striped boxes underneath were made by PCR amplification. Positions of relevant restriction enzyme cleavage sites are indicated. Mo-MuLV env sequences are shown in grey, hFcgRIa sequences in white. Black boxes represent non-coding Mo-MuLV sequences. S, signal peptide; Pro, proline-rich hinge-like region; TM, trans-membrane spanning domain; C, cytoplasmic domain; EC1, EC2, EC3, extracellular domains 1, 2, and 3, each forming one immunoglobulin-like loop.

FIG. 4 shows in vitro immunoglobulin binding by hybrid hFcgRIa/Mo-MuLV env molecules FcRenv-15 and FcRenv-70. Positive and negative protein controls are wild type hFcgRIa (wt-FcR) and irrelevant firefly luciferase proteins, respectively. After in vitro coupled transcription and translation of the DNA sequences encoding these proteins, or a control reaction without DNA template (no DNA) in the presence of $^3$H-labelled leucine, the formed proteins were precipitated with Sepharose beads loaded with IgG2a antibodies. The total reaction product (T), precipitated material (P) and precipitation supernatant (S) were separated through 10% SDS-polyacrylamide gel. The signal in the gel was amplified and exposed to an X-ray film. Extended exposures are indicated with a—above the bands. The molecular weights (MW) of a marker protein mixture is indicated at the right side of the gel.

DETAILED DESCRIPTION OF THE INVENTION

The present invention provides a method to universally exploit a recombinant virus preparation for the targeted delivery of genetic material to many different cell types. To this end, the invention describes methods for the production of recombinant viruses carrying on their surface molecules (members of a specific binding pair) which can specifically interact with a set of secondary molecules (conjugates comprising the counterparts of the members of a specific binding pair). Said secondary molecules possess the ligand specificity for target cell-specific antigens. The indirect binding of the recombinant virus to the target cell via a single secondary molecule, which allows redirection of the same recombinant virus preparation to different target cells depending on the added secondary molecule, is a very important aspect of the invention. Useful secondary molecules to be employed in the invention include immunoglobulins or fragments thereof, chemically modified immunoglobulins or fragments thereof, chemically modified natural protein ligands for target cell antigens, fragments thereof, or recombinant derivatives thereof, and immunoglobulins, fragments thereof, recombinant derivatives thereof, natural protein ligands for target cell antigens, fragments thereof, or recombinant derivatives thereof that are coupled to a peptide motif that can interact with a specific counterpart in suspension. Biotinylation is the paradigm for the chemical modifications which could be employed. Typically, the specificity of the secondary molecules for the target cell antigen is high, and preferably the affinity of the secondary molecules for the target cell antigen is high. Example 1 describes the specific interaction between a cytokine receptor molecule expressed on a mamalian cell surface and a biotinylated cytokine ligand. The invention is not restricted in the range of target cell antigens which could be employed to mediate targeted gene delivery. In principle, any target cell antigen for which a specific secondary molecule is available or can be made available is eligible for application of the invention. It is recognized, however, that not every target cell-specific molecule might serve as an internalization site for viruses bound to it. Furthermore, the efficiency of gene delivery may depend on the composition of the molecular bridge between the virus and the target cell-specific molecule (Etienne-Julan et al., J. Gen. Virol. 73(1992): 3251). Hence, attempts to target gene delivery vehicles to specific cell types relying on methods in which a specific target cell ligand is expressed on the surface of the virus particle, either as a wild-type molecule or as a hybrid with a heterologous protein., can be extremely costly and time-consuming since certain chosen approaches may be destined to fail. The procedures disclosed in this invention, however, allow for comprehensive screening of useful target molecules by employing many different secondary molecules added to the same gene delivery vehicle preparation. Therefore, application of the invention will tremendously increase the chances for successful targeted gene delivery and allow optimization of the procedures at relatively low costs. In addition, standardization and validation of the gene delivery preparations will be simplified as compared to strategies using antibody-antibody or antibody-ligand complexes or methods relying on direct chemical modification of the virus envelope or capsid.

The binding of the secondary molecules to the recombinant viruses is mediated by substances which are exposed on the virus surface and have specific binding capacity for the secondary molecules. Preferably, said substances bind to the secondary molecules with high affinity. Said substances are selected from or contain regions from proteins including but not restricted to Protein A, Protein G, FcR, anti-immunoglobulin scFv, Avidin, Streptavidin, proteins containing structural peptide domains that can specifically interact with a peptide domain counterpart, and recombinant derivatives from the above. Their exposure on the surface of recombinant viruses is envisaged in several ways, which are listed below:

A. for recombinant viruses with an envelope:

Recombinant retroviruses are described in the invention as the paradigm for recombinant enveloped viruses. The invention is, however, not restricted to retroviruses. The invention also applies to other enveloped viruses, such as e.g. rhabdoviruses or herpes viruses.

1. If the binding substance is itself a trans-membrane molecule, e.g. FcR, the complete wild-type binding substance can be expressed on the surface of the retrovirus producing cell line. Alternatively, retrovirus packaging constructs can be expressed in cells naturally expressing the binding substance. Whether these approaches will result in inclusion of the binding substance in the retrovirus particle depends at least in part on the nature of the substance. During the assembly of murine retroviruses at the cell surface cellular membrane molecules are merely excluded from the virus particle, although exceptions have been observed (Závada, J. Gen. Virol. 63(1982): 15; Calafat et al., J. Gen. Virol. 64(1983): 1241). In addition, exclusion of the binding substance from the virus membrane may be overcome by expressing it at very high density on the membrane of the retrovirus producing cell line (Suomalainen and Garoff, J. Virol. 68(1994): 4879).

2. In the application of method no. 1 it is preferred that the trans-membrane binding substance lacks sequences which might elicit intracellular processes in the retrovirus producing cell line or intraviral processes in the virus particle. Such could perhaps occur upon binding of the secondary targeting molecule. Therefore, the binding substance can also be a modified derivative of the wild-type molecule. Modifications include any mutation preventing signal processing through the binding substance. The use of such truncated binding substances is furthermore preferred as to prevent interactions with cellular proteins in the retrovirus producing cell line. It has been suggested that interactions with cytoplasmic proteins might be partially responsible for the exclusion of host cell surface proteins from retrovirus particles (Young et al., Science 250(1990): 1421).

3. Since the fusion process between an infective retrovirus particle and a target cell is assumed to be mediated by an as yet undefined region in the carboxy terminal envelope peptide it can be envisaged that target cell binding according to method no. 1 or 2 might be insufficient to obtain internalization of the gene delivery vehicle into the target cell. Therefore, it may be necessary to co-express the trans-membrane binding substances on the retrovirus surface with wild-type retroviral envelope molecules or segments thereof, which provide the retrovirus with fusion capability. Examples 2 and 3 describe the co-expression of hFcgRIa and wild-type retroviral envelope molecules on the surface of recombinant retrovirus producing cell lines and functional IgG Fc-binding by the exposed hFcgRIa molecules. It is preferred that the co-expressed envelope molecule is incapable of recognizing receptor molecules on cells present in the mixture of cells or in the living animal body subjected to the gene delivery preparation. This can be achieved by employing truncated envelope molecules lacking their receptor recognition site or wild-type envelope molecules from a retrovirus species with a tropism restricted to cells not present in the mixture of cells or in the living animal body subjected to the gene delivery preparation.
4. Hybrid molecules can be made containing (segments of) a binding substance and (segments of) a heterologous protein which anchors the hybrid molecule in the membrane of the retrovirus producing cell line. This method also applies to binding substances which are not themselves trans-membrane proteins. Molecules serving as a membrane anchor can be derived from natural trans-membrane proteins including but not restricted to cytokine or hormone receptors, cell adhesion or interaction molecules, complement receptors, and immunoglobulin receptors. Alternatively, the hybrid molecule could comprise a membrane attachment region from a glycosylphosphatidylinositol-anchored protein. The invention is not restricted to a defined junction site between the heterologous molecules.

5. In the application of method no. 4 it is preferred that the membrane anchor molecule lacks sequences which might elicit intracellular processes in the retrovirus producing cell line or intraviral processes in the virus particle, or interact with cellular proteins in the retrovirus producing cell line. It is, therefore, preferred that sequences conferring the above be deleted from the hybrid binding substance.

Figure 1:
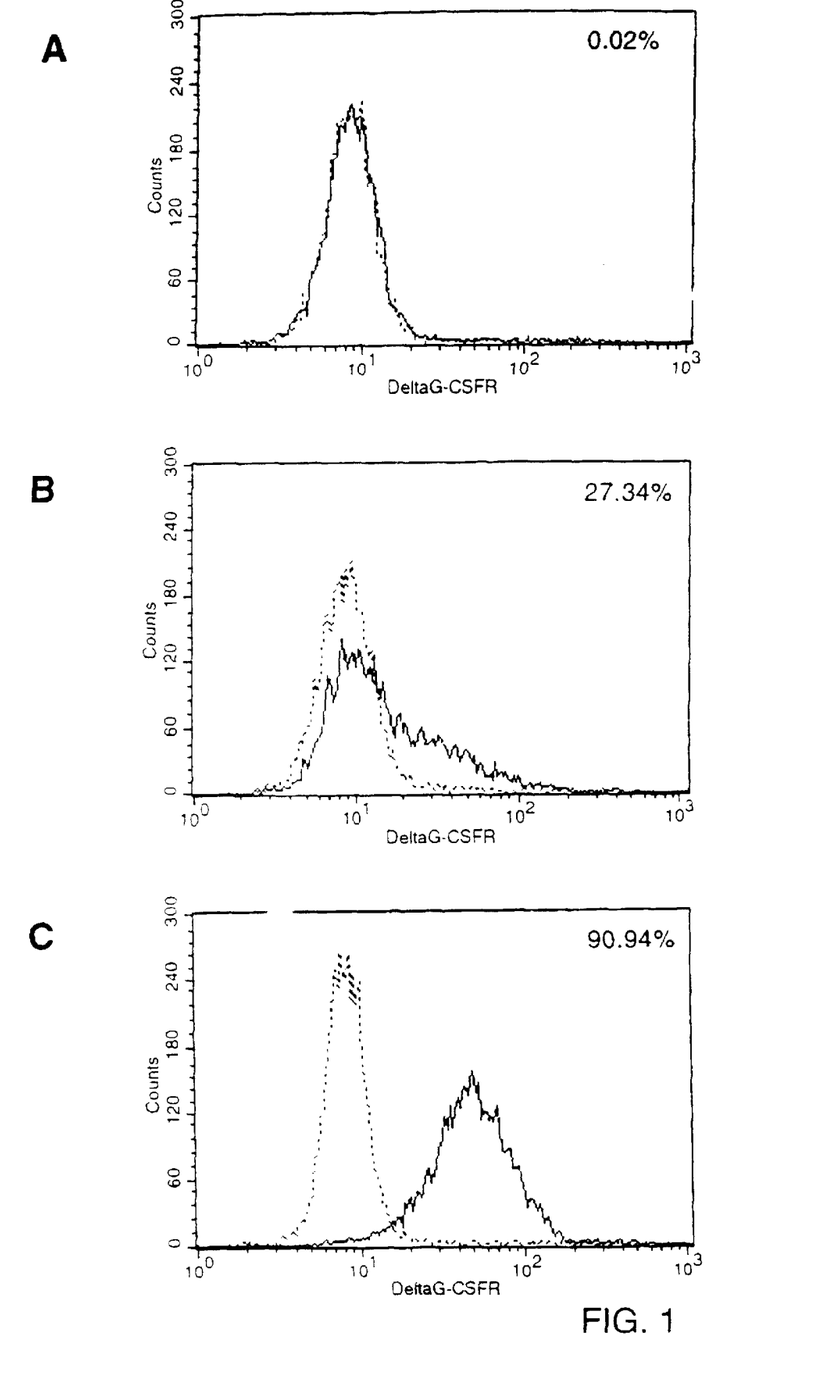

6. Because the retroviral envelope molecule is selectively incorporated in retroviral particles and is assumed to mediate fusion between the virus and the target cell, it is preferred over methods nos. 4 and 5 to construct hybrid molecules containing the retroviral envelope peptide sequences responsible for the above processes and the peptide sequences from the binding substance responsible for binding to the secondary target molecule. Also this method applies to binding substances which are not themselves trans-membrane proteins. The invention is not restricted to a defined junction site between the heterologous molecules. Example 4 describes the construction of two such hybrid binding substances and Example 5 shows that said hybrid binding substances retain functional binding capacity for secondary target molecules.
7. Hybrid molecules can be made containing (segments of) a binding substance and (segments of) a heterologous protein which specifically interacts with extracellular regions of membrane molecules on the retrovirus producing cell surface. Preferably, the hybrid molecule interacts with membrane molecules which are specifically incorporated into retrovirus particles. Typically, these membrane molecules are (segments of) retroviral envelope proteins. This method also applies to binding substances which are not themselves trans-membrane proteins.
8. The expression of viral membrane proteins on the cell surface requires correct folding and assembly in the endoplasmatic reticulum (ER) of the virus producing cell line (reviewed by Doms et al., Virology 193(1993): 545). Retroviral envelope molecules assemble into dimers, trimers, or tetramers, depending on the retrovirus species. Incorrect oligomerization may prevent proper transport to the Golgi apparatus, leading to degradation of the molecule. It can be anticipated that this would be the faith of some hybrid substances produced according to methods nos. 4 to 7. This could possibly be prevented by co-expressing the hybrid substance with wild-type envelope molecules or segments thereof. The formation of hetero-oligomers might ensure correct processing in the ER. The preferred requirements for co-expressed envelope molecules described under no. 3 also apply here.

The principles of methods A 1–8 also apply to pseudotyped viruses in which the envelope glycoproteins from one virus species are carried on the membrane of a heterologous virus species. Such phenotypic mixing of envelope glycoproteins occurs between a variety of different virus families (reviewed by Závada, J. gen. Virol. 63(1982): 15). The invention also applies to enveloped viruses with hybrid envelope proteins, comprising fragments of related or even unrelated viruses. It has, e.g., been shown possible to generate infectious recombinant retroviruses carrying hybrid influenza hemaglutinin/retrovirus envelope proteins (Dong et al., J. Virol. 66(1992): 7374).

B. for viruses with a capsid:

The invention is described for, but not restricted to recombinant adenoviruses and adeno-associated viruses. Hybrid molecules can be made containing (segments of) a binding substance and (segments of) virus capsid proteins. For adenoviruses, it is preferred to locate the binding substance in the head domain of the fiber protein. This domain carries the receptor recognition site and it has been shown possible to change the adenovirus receptor specificity by manipulating this segment (Stevenson et al., J. Virol. 69(1995): 2850). For certain hybrid molecules it may be necessary to co-express the hybrid molecule with wild-type fiber protein to ensure proper fiber trimerization and association with the penton base complex. Alternatively, other capsid proteins of adenovirus may be used to incorporate the binding substance. E.g., Curiel et al. (Hum. Gene Ther. 3(1992): 147) have generated a chimeric serotype 5 adenovirus that contains a *Mycoplasma pneumoniae* P1 protein epitope as part of the hexon protein.

It is furthermore preferred that the natural adenovirus receptor binding sequences be deleted from the hybrid molecule. Hybrid AAV capsid proteins with altered binding specificity are preferably made using (segments of) VP3, since the AAV capsid mainly comprises of this molecule. Alternatively, VP1 or VP2 could be used. The AAV viral proteins allow insertions which are exposed on the capsid surface (unpublished results from the group of Dr. R. Samulski, Univ. of North Carolina, Chapel Hill, N.C.). For certain hybrid molecules it will be necessary to co-express the hybrid molecule with wild-type capsid protein. The invention is not restricted to specific junction sites between the heterologous proteins.

Since many virus capsids self-assemble independent of the presence of viral DNA, empty pseudocapsids can be generated in vitro. Assembly of empty AAV-like particles does not even require all three capsid proteins (Ruffing et al., J. Virol. 66(1992): 6922). Thus, there is significant freedom to design novel pseudocapsids. Empty virus-like particles can be used to package and transfer exogenous non-viral DNA. This has been shown for Polyoma Virus pseudocapsids (Forstová et al., Hum. Gene Ther. 6(1995): 297). Furthermore, exogenous non-viral DNA can be chemically coupled onto the exterior of virus capsids (Curiel et al., Hum. Gene Ther. 3(1992): 147; Cotten et al., Proc. Natl. Acad. Sci. USA 89(1992): 6099). The invention emphatically also applies to the latter two approaches and their combination, i.e. chemical coupling of exogenous DNA to the outer surface of empty capsids.

EXAMPLES

Example 1

Specific Binding of Biotinylated G-CSF to G-CSFR Molecules Expressed on the Surface of Mouse Fibroblasts.

To express receptors for granulocyte-colony stimulating factor (G-CSF) on the cell membrane of murine fibroblasts, PA317 cells (Miller and Buttimore, Mol. Cell. Biol. 6(1986): 2895) were transduced with ecotropic LNCX/GRDcyt virus. The construct pLNCX/GRDcyt (generated in the laboratory of Dr. I. Touw, Erasmus University Rotterdam, The Netherlands) was made by inserting the cDNA sequence for a mutant G-CSF receptor (DG-CSFR) into pLNCX (Miller and Rosman, BioTechniques 7(1989): 980). DG-CSFR differs from the wild-type molecule by an almost complete deletion of the intracellular domain, rendering the receptor incapable of signal-transduction. The extracellular and trans-membrane domains of DG-CSFR are of wild-type structure. DG-CSFR exhibits, therefore, normal binding capacity for its cytokine ligand. Transduced PA317 cells were isolated by selecting for resistance to 1 mg/ml G418 (Geneticin; Gibco, Paisley, UK), conferred by expression of the neo$^r$ gene in LNCX/GRDcyt. Resistant PA317 cells were incubated with biotinylated G-CSF. Bound G-CSF was visualised on a Fluorescence Activated Cell Sorter (FACS) after incubation with PE-conjugated Streptavidin (Molecular Probes, Eugene, OR), biotinylated goat-anti-Streptavidin antibodies (Vector Laboratories, Burlingame, Calif.), and a second incubation with PE-Streptavidin. As can be seen in FIG. 1, untransduced PA317 cells did not bind any biotinylated G-CSF, whereas approximately 27% of the transduced cells bound G-CSF. After FACS sorting of positive cells and cloning by limiting dilution, a clone was isolated which strongly bound biotinylated G-CSF (FIG. 1C). This example shows that a biotinylated cytokine specifically binds to its natural receptor expressed on the membrane of a mammalian cell line.

Example 2

Generation of Recombinant Retrovirus Packaging Cell Lines Expressing hFcgRIa Proteins on their Cell Membrane.

For expression of functional hFcgRIa on the surface of retrovirus packaging cell lines the construct pRc/CMV-hFcgRIa was used. This construct was generated by inserting a 1.3 kb HindIII-NotI fragment including the full-length p135 hFcgRIa-cDNA sequence (Allen and Seed, Science 243(1989): 378, GenBank accession number M21090) from clone CDM into the polylinker of pRc/CMV. Twenty microgram pRc/CMV-hFcgRIa was transfected onto the ecotropic packaging cell line GP+E-86 (Markowitz et al., J. Virol. 62(1988): 1120) and onto the amphotropic packaging cell line PA317, according to the method described by Chen and Okayama (Mol. Cell. Biol. 7 (1987): 2745). Transfectants were selected for resistance to 1 mg/ml G418, conferred by expression of the SV40pr-neo$^r$-p(A) casette on the pRc/CMV-hFcgRIa construct. Pools of resistant cells were analysed for hFcgRIa expression on a FACS, after staining with the anti-FcgRI monoclonal antibody (MoAb) 22 (Guyre et al., J. Immunol. 143(1989): 1650) and FITC-conjugated goat-anti-mouse IgG antibodies (GaM-FITC; Becton Dickinson Immunocytometry Systems, San Jose, Calif. [BDIS]). Table 1 shows that only few G418-resistant GP+E-86 cells (E86FcR) and G418-resistant PA317 cells (PAFcR) were found to express FcgRI on their surface. FcgRI-expressing cells were sorted using the FACS and expanded. After two weeks of culture, the sorted populations were analysed for FcgRI-expression as before. As can be seen in table 1, the sorting procedure resulted in significantly enriched FcgRI-expressing E86FcR and PAFcR cell populations.

TABLE 1

FcgRI Expression on pRc/CMV-hFcgRIa Transfected and FACS Sorted Ecotropic and Amphotropic Recombinant Retrovirus Packaging Cell Lines.

| Packaging Cells | FcRI Positive Cells (%)[1] | Average FcgRI Expression[2] |
| --- | --- | --- |
| GP + E-86 | 0.1 | N.D. |
| PA317 | 0.2 | 0.98 |
| E86FcR | 0.9[3] | N.D. |
| E86FcR sorted | 16.4 | 1.16 |
| PAFcR | 7.6[3] | N.D. |
| PAFcR sorted-315[4] | 10.5 | 1.43 |
| PAFcR sorted-216[4] | 20.5 | 2.37 |

[1]Percentage cells exhibiting FITC fluorescence following incubation with MoAb 22 and GaM-FITC. Controls incubated with GaM-FITC only were set to ≦ 0.1%.
[2]Relative median FITC fluorescence after incubation with MoAb 22 and GaM-FITC as compared to incubation with irrelevant anti-KLH isotype control MoAb (BDIS) and GaM-FITC.
[3]Average of two independent measurements.
[4]PAFcR cells were subjected to two independent sorting experiments.
N.D., not done.

Figure 2:
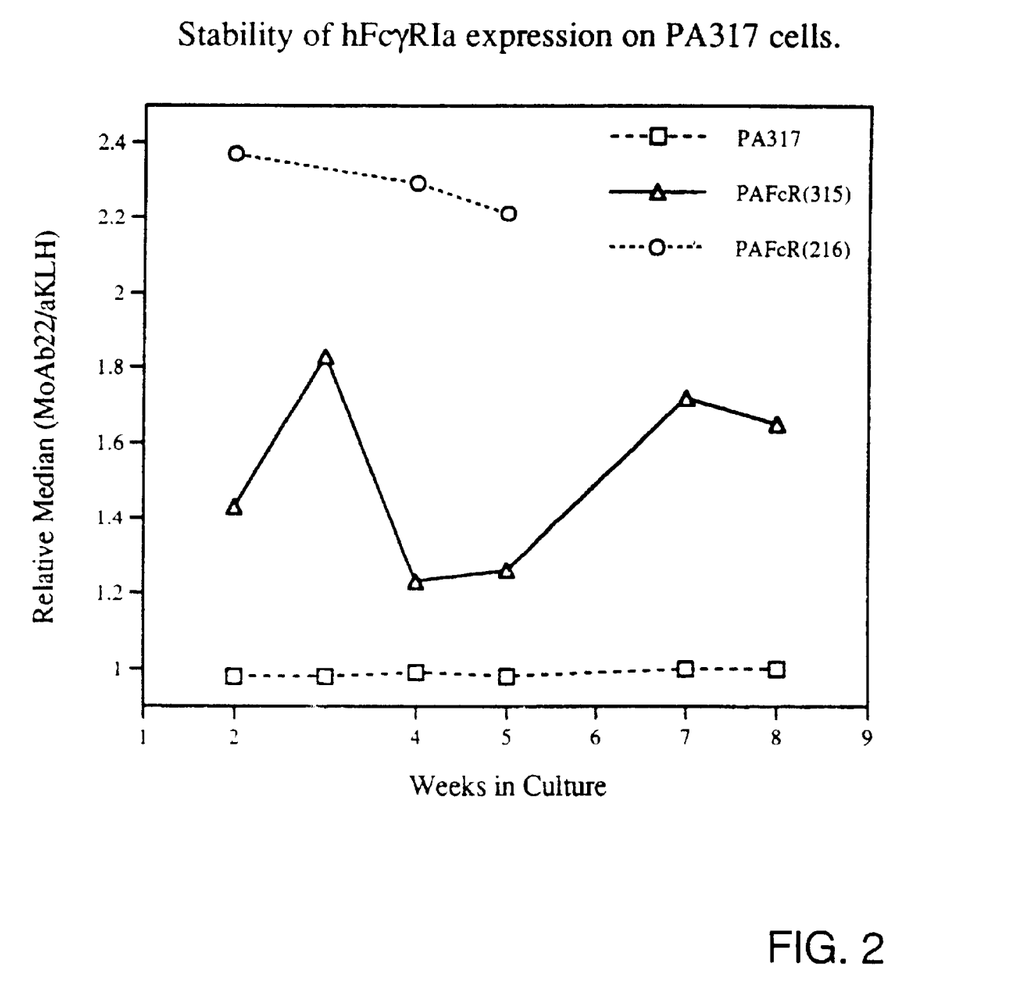
FIG. 2 depicts the levels of hFcgRIa expression on the membrane of PA317 cells during in vitro culture for up to eight weeks. Unmanipulated PA317 cells, and two mixed populations of transfected PA317 cells which were FACS sorted for hFcgRIa expression (PAFcR sorted-315 and PAFcR sorted-216) were stained with the anti-FcgRI MoAb 22 or with an irrelevant anti-KLH isotype control. The ratios between the median signal intensities after staining with MoAb 22 over the control are given.

To study whether hFcgRIa remained stably expressed on the packaging cell surface in the absence of g-chain co-expression, two sorted cell populations expressing different levels of hFcgRIa as deduced from their median FITC-signals after staining with MoAb 22 as compared to staining with irrelevant isotype controls, were cultured for up to eight weeks in culture medium containing G418. Regular reanalysis showed rather stable median fluorescence signals (approx. 1.5 and 2.3 for the two sorted populations, as compared to 1.0 for untransfected PA317 cells; FIG. 2) throughout the observation period.

Immunophenotypic analysis of wild-type hFcgRIa revealed three distinct epitopes, one of which comprises the Fc-binding domain (Guyre et al., J. Immunol. 143(1989): 1650). One of the sorted cell populations was analysed using the directly FITC-stained MoAbs 22 and 32.2 (Medarex, Annandale, N.J.), which each define one of the two non-Fc-binding epitopes. Table 2 shows that both MoAbs recognized the hFcgRIa molecule exposed on the cell surface. The increase in fluorescence which was observed when both MoAbs were combined demonstrate that they bind to distinct epitopes on the packaging cell surface. Pre-incubation of the cells with irrelevant unstained mouse immunoglobulins of IgG1 or IgG2a isotype (BDIS) did not influence the binding of MoAbs 22 and 32.2 (not shown). These results demonstrate that hFcgRIa of correct immunophenotypic structure was expressed on the cell surface of a retrovirus packaging cell line.

TABLE 2

Immunophenotype Analysis of Amphotropic Packaging Cells Expressing hFcgRIa.

| FITC-labeled MoAb | % Positive Cells | Mean Fluorescence Intensity (a.u.) |
| --- | --- | --- |
| anti-KLH (irrelevant) | 0.9[1] | 15.0 |
| anti-hFcgRIa MoAb 22 | 13.0 | 64.6 |
| anti-hFcgRIa MoAb 32.2 | 8.1 | 46.3 |
| anti-hFcgRIa MoAbs 22 + 32.2 | 21.1 | 105.8 |

PAFcR sorted-216 cells were incubated with the indicated FITC-labeled MoAbs and analysed on a FACS. [1] The treshold for a positive score was set at ≧99% negative cells on the anti-KLH-FITC stained sample.
Ecotropic and amphotropic hFcgRIa-expressing populations were cloned by limiting dilution. Twelve individual E86FcR and eleven individual PAFcR clones were expanded and analysed for hFcgRIa-expression. The two clones expressing the highest level of hFcgRIa from each population were used co investigate whether hFcgRIa-expression on the cell surface of packaging cells influences the retrovirus production. To this end, cell-free supernatant was harvested from these four clones as well as from the parental packaging cell lines under standard conditions (72 hours at 32° C. in 10 ml alpha-modified DMEM with 10% BCS per 80 cm² confluent cell monolayer). The supernatants were analysed for reverse transcriptase activity (Goff et al., J. Virol. 38(1981): 339), in a two-fold dilution titration. Comparison of the radiation intensity of incorporated $^{32}$P-dTrPs by exposure to X-ray film revealed that expression of hFcgRIa did not influence the shedding of virus particles into the culture medium more than a factor 2.3 (table 3).

TABLE 3

Retrovirus Particle Production by Packaging Cell Lines Expressing hFcgRIa.

| Packaging Cell Line | FcgRI Expression[1] | Retrovirus Production[2] |
| --- | --- | --- |
| PA317 | 1.2 | (1) |
| PAFcR-2 | 2.3 | 2.0 |
| PAFcR-8 | 2.7 | 2.0 |
| GP + E-86 | N.D. | 1.8 |
| E86FcR-3 | 2.8 | 0.8 |
| E86FcR-14 | 2.6 | 1.3 |

[1]Relative median fluorescence signal after staining with FITC-labeled MoAbs 22 + 32.2 as compared to anti-KLH-FITC.
[2]The RT-activity in the culture supernatant is given relative to the RT-activity shed by PA317 cells.
N.D., not done.

Example 3

Immunoglobulin Binding by hFcgRIa Proteins Expressed on the Cell Membrane of Recombinant Retrovirus Packaging Cell Lines.

To test whether hFcgRIa expressed on the surface of retrovirus packaging cells is capable of specific immunoglobulin-Fc binding, PAFcR sorted-315 cells were incubated with irrelevant mouse immunoglobulins of IgG1 or IgG2a isotype. FcgRI molecules should bind IgG2a molecules with high affinity and IgG1 molecules with low affinity. As can be seen in table 4, approximately one third of the sorted cells were expressing low amounts of hFcgRIa, as indicated by MoAb22-staining with low relative median signal. All hFcgRIa molecules on PAFcR cells also bound mouse IgG2a (similar percentage positive cells and signal intensity), whereas mouse IgG1 was hardly bound. On human primary monocytes, which were used as a positive control, hFcgRIa molecules were strongly expressed and specifically bound mouse IgG2a immunoglobulins. The capacity of hFcgRIa molecules on monocytes to bind immunoglobulins, however, was lower than measured on pRc/CMV-hFcgRIa transfected packaging cells (55% of MoAb22-positive monocytes bound IgG2a, with a much lower signal intensity). In conclusion, all hFcgRIa molecules characterised by MoAb22-binding expressed on the surface of PAFcR cells exhibit a correct structure for specific high affinity binding of immunoglobulins.

TABLE 4

Immunoglobulin-Fc Binding by FcgRI Expressed on PA317 Cells

| Primary MoAb | Human Monocytes | | PA317 | | PAFcR sorted-315 | |
| --- | --- | --- | --- | --- | --- | --- |
| | % Pos. | Rel. Med[1] | % Pos. | Rel. Med. | % Pos. | Rel. Med. |
| none | 0.8 | (1) | 0.9 | (1) | 0.8 | (1) |
| irr-IgG1 | 0.7 | 1.84 | 0.6 | 0.96 | 6.2 | 1.15 |
| irr-IgG2a | 35.1 | 3.69 | 0.4 | 0.95 | 30.6 | 1.61 |
| MoAb22 | 64.2 | 8.82 | 0.5 | 0.94 | 33.0 | 1.65 |

Human primary monocytes, PA317 cells, or a pool of pRc/CMV-hFcgRIa transfected PA317 cells partially expressing hFcgRIa (PAFcR sorted-315) were first incubated with MoAb22 (IgG1 isotype), anti-KLH IgG1, anti-KLH IgG2a, or PBS/1% BSA ("none"), followed by an incubation with GaM-FITC. The percentage positive cells and the median fluorescence intensities were determined on a FACS.
[1] Relative median fluorescence intensity of cells incubated with indicated primary MoAb and GaM-FITC as compared to cells incubated with GAM-FITC alone.

Example 4

Construction of Hybrid hFcgRIa/Mo-MuLV Envelope Genes.

Figure 3:
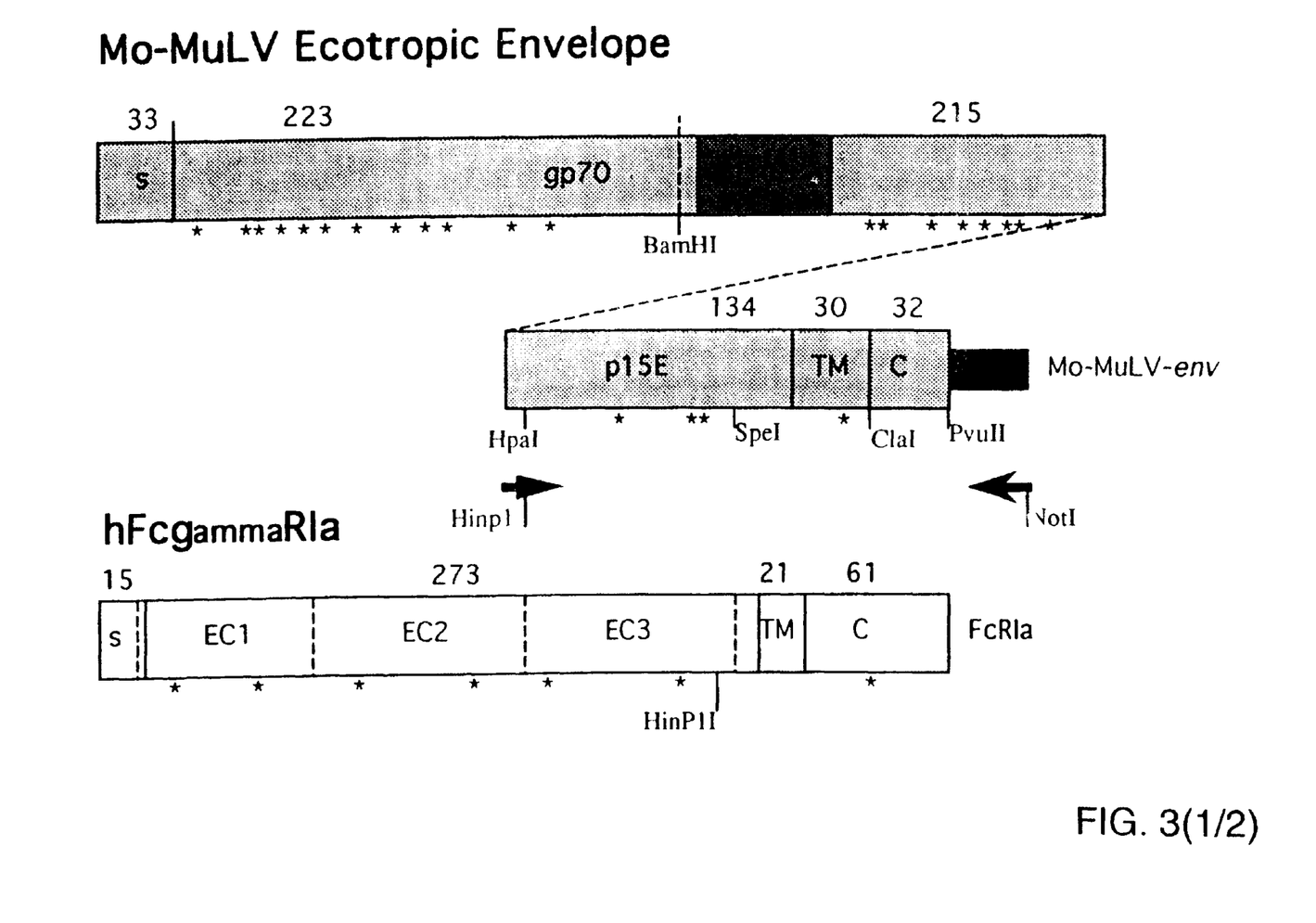
Figure 4:
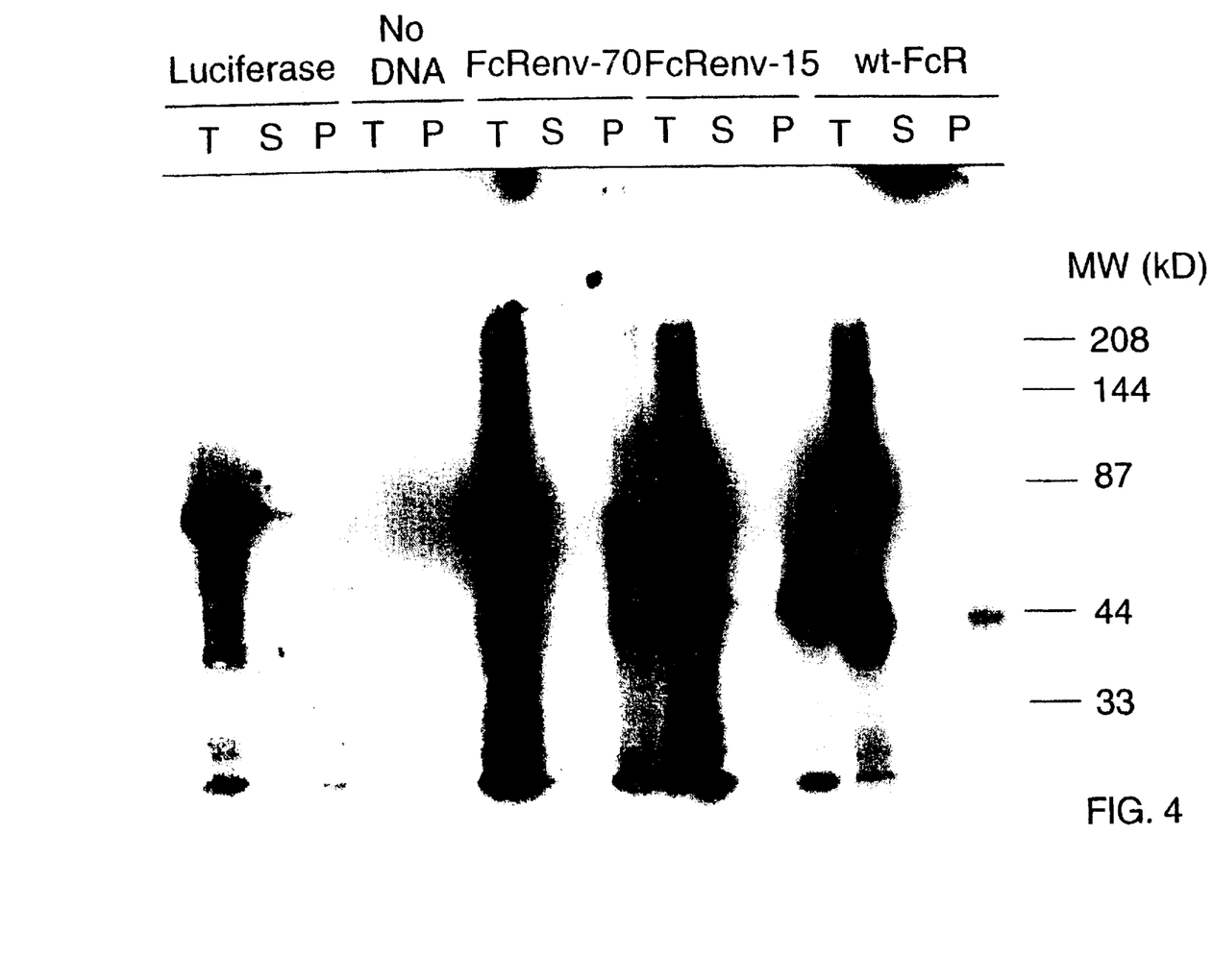

For the construction of hybrid molecules with immunoglobulin-binding properties of hFcgRIa and virus-incorporation and membrane-fusion properties of envelope glycoprotein, pRc/CMV-hFcgRIa (see above) was used in combination with Mo-MuLV env sequences (Shinnick et al., Nature 293(1981): 543) Two different hybrid hFcgRIa/Mo-MuLV-env constructs were made (FIG. 3). In both constructs, 3' hFcgRIa sequences in the pRc/CMV-hFcgRIa construct were replaced by 3' Mo-MuLV env sequences. Both constructs contain p135 sequences from the leader sequence to the HinPlI-site at position 849–852. This fragment comprises the three extracellular domains of hFcgRIa, excluding the 61 carboxy terminal nucleotides. In hybrid construct pRc/CMV-FcRenv-15, the p135-fragment is coupled to p15E env sequences encoded by a fragment starting from the HpaI-site at position 7195–7200 of Mo-MuLV until position 7823 in the IR sequence of the 3'LTR. To this end, the HpaI-site was converted to a HinPlI-site by PCR, and a NotI-site was introduced in the 3'LTR by PCR. An internal SpeI-PvuII fragment (nt 7487–7747) was exchanged for cloned sequences. The correct sequence of the hFcgRIa/Mo-MuLV-env junction and of all sequences generated by PCR was confirmed by sequencing. Hybrid gene FcRenv-15 encodes an in-frame fusion protein comprising the extracellular domains of hFcgRIa until an Arg-residue 12 aminoacids downstream from the 3' Cys-residue forming the third immunoglobulin-like extracellular loop and all but the five most 5' p15E aminoacids. To generate hybrid construct pRc/CMV-FcRenv-70, the HinPlI-site from the 5' p135-fragment was made blunt-end and was ligated to a BamHI (position 6537–6542)-PvuII (position 7745–7750) fragment of Mo-MuLV, after the BamHI-site was made blunt-end, and the 3' PvuII-NotI PCR-fragment from pRc/CMV-FcRenv-15. Ligation of the blunt-end HinPlI and BamHI-sites restored the BamHI-site. The correct structure of the hFcgRIa/Mo-MuLV-env junction was confirmed by sequencing. Hybrid gene FcRenv-70 comprises the same hFcgRIa-fragment as described for pRc/CMV-FcRenv-15 coupled to the Mo-MuLV env sequences starting from an Ile-residue at the BamHI-site in the amino terminal domain of gp70 and including the complete proline-rich hinge-like region and carboxy terminal domain of gp70 and the complete p15E peptide.

On Jul. 24, 1996, the applicants have deposited with the European Collection of Cell Cultures (ECACC), Salisbury, Wiltshire, U.K., the plasmid pRc/CMV-FcRenv-15, given ECACC accession number P96072515, and plasmid pRc/CMV-FcRenv-70, given ECACC accession number P96072514. These deposits were made under the provisions of the Budapest Treaty on the International Recognition of the Deposit of Microorganisms for the purposes of patent procedure and the regulations thereunder.

Example 5

Hybrid hFcgRIa/Mo-MuLV Envelope Genes FcRenv-15 and FcRenv-70 Encode Proteins of Correct Molecular Weight that have Immunoglobulin Binding Capacity To test whether the fusion genes FcRenv-15 and FcRenv-70 encode functional hybrid molecules with immunoglobulin binding properties, the pRc/CMV-FcRenv-15 and pRc/CMV-FcRenv-70 constructs (Example 4) were used as templates for coupled in vitro transcription and translation. Transcription was initiated at the T7 promoter upstream of the gene insertion in the pRc/CMV vector. One microgram pRc/CMV-FcRenv-15 or pRc/CMV-FcRenv-70 DNA was added to a 25 microliter leucine-free T7 TnT coupled reticulocyte lysate reaction mixture (Promega, Madison, Wis.) with 20 units RNasin ribonuclease inhibitor (Promega) and 20 microCi $^3$H-leucine (Amersham, Buckinghamshire, UK). The reaction was allowed to proceed for 120 minutes at 30° C. according to the guidelines provided by the manufacturer. Control reactions were performed without DNA template, with an irrelevant control DNA template (firefly luciferase control DNA provided with the T7 TnT coupled reticulocyte lysate system), and with positive control pRc/CMV-hFcgRIa encoding wild-type hFCgRIa. To 5 microliter of the reaction mixture, 20 microliter SDS-PAGE loading buffer (to a final concentration of 62.5 mM Tris pH 6.8, 10% glycerol, 2% beta-mercaptoethanol, 0.5% SDS, 0,0025% bromo phenol blue) was added. The remaining 20 microliter was diluted with 180 microliters of precipitation buffer (10 mM Tris-HCl pH 7.5, 150 mM NaCl, 5 mM EDTA, 1% Triton-100 with protease inhibitors PMSF at 0.1 mM, aprotinin at 10 microgram/ml, pepstatin at 5 microgram/ml, trypsin inhibitor at 10 microgram/ml, and leupeptin at 10 microgram/ml). Next, 10 microliter KLH-aKLH-IgG2a-Sepharose slurry was added and mixed by tilted rotation for 90 minutes at room temperature. Said slurry was prepared according to the following procedure. First, 16.4 mg Keyhole Limpet Hemocyanin (KLH; Sigma, St. Louis, Mo.) was coupled at 1.8 mg/ml to 1 gram CNBr-activated Sepharose 4B (Pharmacia Biotech, Uppsala, Sweden) according to the manufacturers instructions. The KLH-Sepharose product was stored in PBS with 0.002% sodium azide at 4° C. Next, KLH-Sepharose was mixed 1:1 with 50 microgram/ml anti-KLH-IgG2a monoclonal antibody (Beckton-Dickinson Immunocytometry Systems, San Jose, Calif.) and incubated for 30 minutes at room temperature. Finally, the KLH-aKLH-IgG2a-Sepharose beads were washed two times in 20 volumes PBS. This procedure should result in Sepharose beads coated with immunoglobulins of the IgG2a isotype that have their Fc domain projecting outwards. After incubation of the in vitro transcribed and translated reaction product with KLH-aKLH-IgG2a-Sepharose, the KLH-aKLH-IgG2a-Sepharose beads were spun down and the precipitation supernatant was removed. To 5 microliter precipitation supernatant 20 microliter SDS-PAGE loading buffer was added as above. The pelleted KLH-aKLH-IgG2a-Sepharose beads were washed 6-times in 1 ml precipitation buffer. After a final spin, 25 microliter SDS-PAGE loading buffer was added to the pellet. The above described procedure resulted in three different samples of each coupled in vitro transcription-translation reaction, i.e., the total reaction product, the immunoglobulin bound precipitated product, and the remaining material in the precipitation supernatant. Ten microliters of these samples were heated at 85° C. for 2 minutes and subsequently separated by SDS-PAGE through a 10% gel according to standard procedures (Laemmli, Nature 227(1970): 680). After separation, the proteins in the gel were fixed in water/isopropanol/acetic acid (65%/25%/10% vol.) for 30 minutes at room temperature and thereafter incubated for 15 minutes at room temperature in Amplify (Amersham) for fluorographic enhancement of the signal. Finally, the gel was dried for 90 minutes at 80° C. under vacuum and exposed to X-ray film with an enhancing screen. Figure no. 5 shows the result of this experiment. As can be seen, the constructs with genes encoding wild-type hFcgRIa or hFcgRIa/Mo-MuLV envelope fusion molecules all expressed proteins exhibiting a migration pattern corresponding to their predicted molecular weights, i.e., 42.5 kD for hFcgRIa, 52 kD for FcRenv-15, and 75,6 kD for FcRenv-70. The latter gene furthermore encodes a smaller protein product. This molecule perhaps represents the approximately 60 kD proteolytically processed protein after release of the p15E peptide. As can furthermore be seen in Figure no. 5, all these protein products were precipitated by KLH-aKLH-IgG2a-Sepharose beads, in contrast to the irrelevant control protein luciferase, demonstrating that the immunoglobulin binding property of wild-type hFcgRIa is retained after fusion of the three extracellular domains of hFcgRIa to Mo-MuLV envelope sequences.

What is claimed is:

1. A targeting gene delivery vehicle complex, said targeting gene delivery vehicle complex comprising:

a gene delivery vehicle coupled with a bispecific conjugate, said gene delivery vehicle comprising:

an expressible recombinant nucleic acid molecule encoding a gene product of interest;

a capsid or an envelope having an exterior, said capsid or envelope enveloping said recombinant nucleic acid molecule; and a first member of a specific binding pair associated with said capsid or envelope exterior, which member of said specific binding pair is not directly associated with a surface of a target cell and wherein said first member of the specific binding pair is naturally or recombinantly expressed on said capsid or envelope exterior;

wherein said bispecific conjugate comprises a second member of said specific binding pair covalently coupled to a targeting moiety capable of binding to a target molecule associated with the surface of the target cell.

* * * * *

UNITED STATES PATENT AND TRADEMARK OFFICE
CERTIFICATE OF CORRECTION

PATENT NO. : 6,261,554 B1
DATED : July 17, 2001
INVENTOR(S) : Domenico Valerio and Victor Willem van Beusechem It is certified that error appears in the above-identified patent and that said Letters Patent is hereby corrected as shown below:

Column 2,
Line 14, change "extend" to -- extent --

Column 3,
Line 30, delete the comma after "vitro,"

Column 4,
Line 9, change "vehcle" to -- vehicle --

Column 5,
Line 20, change "paret" to -- part --

Column 7,
Line 16, change "(i994)" to -- (1994) --
Line 48, change "strepatavidin" to -- streptavidin --

Column 10,
Line 48, change "a – above" to -- a "–" above --

Column 11,
Line 18, change "mamalian" to -- mammalian --
Line 33, delete the period after "protein"

Column 16,
Line 64, change "treshold" to -- threshold --

UNITED STATES PATENT AND TRADEMARK OFFICE
CERTIFICATE OF CORRECTION

PATENT NO. : 6,261,554 B1
DATED : July 17, 2001
INVENTOR(S) : Domenico Valerio and Victor Willem van Beusechem It is certified that error appears in the above-identified patent and that said Letters Patent is hereby corrected as shown below:

Column 17,
Line 13, change "$^{32}$P-dTrPs" to -- $^{32}$P-dTTPs --

Signed and Sealed this

Sixteenth Day of September, 2003

JAMES E. ROGAN
*Director of the United States Patent and Trademark Office*